United States Patent
Pan et al.

(10) Patent No.: US 10,494,589 B2
(45) Date of Patent: *Dec. 3, 2019

(54) METHOD FOR INDICATING TIME FOR WASHING OR INDICATING DELIVERY OF ANTIBACTERIAL AGENT

(71) Applicant: Colgate-Palmolive Company, New York, NY (US)

(72) Inventors: Long Pan, Cherry Hill, NJ (US); Shaotang Yuan, East Brunswick, NJ (US); Jairajh Mattai, Hillsborough, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 173 days.

This patent is subject to a terminal disclaimer.

(21) Appl. No.: 13/944,208

(22) Filed: Jul. 17, 2013

(65) Prior Publication Data

US 2014/0170086 A1 Jun. 19, 2014

Related U.S. Application Data

(63) Continuation-in-part of application No. PCT/US2012/070505, filed on Dec. 19, 2012.

(51) Int. Cl.
| | |
|---|---|
| *C11D 3/16* | (2006.01) |
| *C11D 17/08* | (2006.01) |
| *A61K 8/27* | (2006.01) |
| *A61K 8/44* | (2006.01) |
| *A61Q 19/10* | (2006.01) |

(52) U.S. Cl.
CPC .............. *C11D 3/168* (2013.01); *A61K 8/27* (2013.01); *A61K 8/44* (2013.01); *A61Q 19/10* (2013.01); *C11D 17/08* (2013.01); *A61K 2800/45* (2013.01); *A61K 2800/58* (2013.01)

(58) Field of Classification Search
CPC .......... C11D 17/08; C11D 3/168; A61K 8/27; A61K 2800/58; A61K 2800/45; A61K 8/44; A61Q 19/10
See application file for complete search history.

(56) References Cited

U.S. PATENT DOCUMENTS

| | | | |
|---|---|---|---|
| 4,339,432 A | 7/1982 | Ritchey et al. | |
| 4,565,693 A | 1/1986 | Marschner | |
| 5,061,815 A | 10/1991 | Leu | |
| 5,911,978 A | 6/1999 | Carr et al. | |
| 6,607,711 B2 | 8/2003 | Pedersen | |
| 7,226,584 B2 | 6/2007 | Lersch et al. | |
| 7,442,674 B2* | 10/2008 | Polonka | C11D 3/1213 424/70.1 |
| 2004/0033916 A1* | 2/2004 | Kuzmin et al. | 510/161 |
| 2007/0183989 A1 | 8/2007 | Gaffar et al. | |
| 2010/0266480 A1 | 10/2010 | Huang | |
| 2010/0330163 A1* | 12/2010 | Soparkar | 424/450 |
| 2011/0229536 A1 | 9/2011 | Kvitnitsky et al. | |

FOREIGN PATENT DOCUMENTS

| | | |
|---|---|---|
| CN | 101606639 | 12/2009 |
| EP | 0842664 | 5/1998 |
| EP | 1064946 | 1/2001 |
| JP | S57-158724 | 9/1982 |
| WO | 1994/024998 | 11/1994 |
| WO | WO 2012/087288 A2 | 6/2012 |

OTHER PUBLICATIONS

Bishop et al., J. Phys. Chem. B 2009, 113, 1413-1417.*
International Search Report and Written Opinion for International Application No. PCT/US2013/050845 dated Aug. 13, 2014.
Deschaume et al., 2008, "Interactions of aluminum hydrolytic species with biomolecules," New J. Chem. 32:1346-1353.
Liu et al., 2000, "The research on zinc coordination number 5 odd structure in zinc complex with L-lysine," J. Mol. Sci. 16(2):114-117.
Schmetzer et al., 1985, "Wulfingite, $\epsilon$-Zn(OH)2, and simonkolleite, Zn5(OH)8C12 H2O, two new minerals from Richelsdorf, Hesse, F.R.G.," N. Jb. Miner. Mh. 4:145-154.
Zhu et al., 1990, "Synthesis and crystal structure of [Zn+{H2N(CH2)4CH(NH2)COONa}2SO4−]• H2O," Chinese Science Bulletin 35(18):1521-1525.
Hartwell, et al., "Preparation and Characterization of Tyrosine and Lysine Metal Chelate Polyesters and Polyamides," Journal of the American Chemical Society, vol. 92, No. 5, pp. 1284-1289.
Moorer et al., 1982, "Antibacterial activity of gutta-percha cones attributed to the zinc oxide component," Oral Surgery 53(5): 508-517.

* cited by examiner

*Primary Examiner* — Robert S Cabral

(57) ABSTRACT

A method for indicating release of an antibacterial agent or for indicating an amount of time for cleansing skin with an aqueous cleansing composition comprising a surfactant and a zinc X halide complex, wherein X is an amino acid or trimethylglycine, wherein the method comprises washing skin with the cleansing composition and water for a time until the zinc X halide complex precipitates from the aqueous cleansing composition.

11 Claims, No Drawings

METHOD FOR INDICATING TIME FOR WASHING OR INDICATING DELIVERY OF ANTIBACTERIAL AGENT

CROSS REFERENCE TO RELATED APPLICATIONS

This application is a continuation-in-part of Application No. PCT/US2012/070505, filed on 19 Dec. 2012, which is incorporated herein by reference.

BACKGROUND OF THE INVENTION

Visual and sensory triggers are sometimes incorporated into personal care products, such as liquid hand soaps (LHS), for aesthetic reasons or as indicator of the completion of the washing/rinsing process.

There is a need for alternative approaches for indicating timing for washing or indicating delivery of an antibacterial agent while providing additional benefits.

BRIEF SUMMARY OF THE INVENTION

The invention provides a method for indicating release of an antibacterial agent or for indicating an amount of time for cleansing skin with an aqueous cleansing composition comprising a surfactant and a zinc X halide complex, wherein X is an amino acid or trimethylglycine, wherein the method comprises washing skin with the cleansing composition and water for a time until the zinc X halide complex precipitates from the aqueous cleansing composition. Trimethylglycine as used throughout refers to N,N,N-trimethylglycine.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The method comprises washing with an aqueous composition that contains a surfactant and the zinc X halide complex until the zinc X halide complex precipitates from the aqueous cleaning composition. The time can be 10 to 60 seconds, optionally, 10 to 30 seconds, 10 to 20 seconds, or 15 to 20 seconds.

An unusual and unexpected property of zinc X halide complexes is that the complex is soluble and stable in concentrated aqueous solution, even at neutral pH, making it suitable for formulation in carriers which are gentle on the skin, but as the amount of water increases, rather than remaining in solution as the solution becomes more dilute, as would typically be the case for an ionic complex, the zinc X halide complex hydrolyzes, to provide a relatively insoluble zinc salt, such as zinc oxide, precipitate, thereby permitting controlled deposition of zinc salt on the skin. Certain zinc salts, such as zinc oxide, are antibacterial, and so helps to reduce the presence of pathogenic bacteria on the skin, as well as helping to protect the skin from sun damage. The deposition of the zinc salt on skin will indicate that the zinc salt (an antibacterial agent) has been delivered.

For example, in one embodiment, the zinc X halide is incorporated into a conventional commercial liquid hand soap (LHS) formulation. In certain embodiments, the cleansing composition is nonionic, and optionally free of anionic surfactants. The complex is found to be compatible with the formula and generates a transparent solution. Upon dilution, however, the complex/LHS combination instantly forms a white precipitate. Thus, complex in a nonionic base can be used as a visual/sensory trigger for the washing process. The precipitate, composed of zinc salt, such as ZnO, is deposited on skin and thus enhances the antimicrobial effect of the LHS. Thus zinc amino acid complex in a LHS base can provide both visual/sensory effects as well as antimicrobial and sunscreen benefits to a nonionic LHS formulation.

The invention further provides a method of reducing sun damage to the skin or protecting the skin from sunburn or sun damage, comprising washing the skin with the aqueous cleansing composition and water, prior to exposure to the sun.

The combination of the zinc, the amino acid, and the halide forms a cationic complex-halide salt. The zinc X halide is a water soluble complex formed from the halide acid addition salt of zinc (e.g., zinc chloride) and an amino acid, or from the halide acid addition salt of an amino acid (e.g., lysine hydrochloride) and zinc ion source, e.g., zinc oxide or TBZC, and/or from combination of all three of a halogen acid, an amino acid, and a zinc ion source.

The zinc ion source for combination with an amino acid hydrohalide or an amino acid plus halogen acid may be any source that provides $Zn^{2+}$ ions efficiently, for example zinc oxide, zinc chloride, tetrabasic zinc chloride, zinc carbonate, zinc nitrate, zinc citrate, and zinc phosphate. Zinc oxide is a white powder, insoluble in water. Tetrabasic zinc chloride (TBZC) or zinc chloride hydroxide monohydrate is a zinc hydroxy compound with the formula $Zn_5(OH)_8Cl_2.H_2O$, also referred to as basic zinc chloride, zinc hydroxychloride, or zinc oxychloride. It is a colorless crystalline solid insoluble in water. Both of these materials are found to be soluble in water in the presence of an amino acid and provide a source of zinc ions while restricting the available anions, as an excess of anions can interfere with the complex formation.

The amino acid source can be any amino acid. Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid.

In some embodiments, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine. Neutral amino acids, such as glycine, and even acidic amino acids, such as aspartic acid, however, are also capable of forming salts with strong acids, such as halogen acids. In some embodiments the amino acid is a neutral or acidic amino acid, e.g., glycine.

The halide source can be part of the zinc source, such as zinc chloride or tetrabasic zinc chloride. The halide source can be part of the amino acid, such as an amino acid hydrohalide. Also, the halide source can be a halogen acid. The halide may be chloride, bromide, or iodide, most typically chloride. The acid addition salt of an amino acid and a halogen acid (e.g., HCl, HBr, or HI) is sometimes referred to herein as an amino acid hydrohalide. Thus one example of an amino acid hydrohalide is lysine hydrochloride. Another is glycine hydrochloride.

In certain embodiments, the amount of zinc X halide in the composition is 0.05 to 40% by weight of the composition. In certain embodiments, precursors, e.g., zinc oxide and amino acid hydrohalide, are present in amounts such that when combined into the zinc X halide, the zinc X halide would be present in an amount of 0.05 to 40% by weight of the composition. In either of these embodiments, the amount of the zinc X halide can be varied for the desired purpose, such as an antibacterial agent or as an antiperspirant. In other embodiments, the zinc X halide is present in an amount of 0.05 to 40% by weight of the composition, optionally at least 0.1, at least 0.2, at least 0.3, at least 0.4, at least 0.5, at least 1, at least 2, at least 3, or at least 4 up to 40% by weight of the composition, or, optionally, 0.1 up to 30%, up to 20%, up to 10%, up to 5%, up to 3%, up to 2%, or up to 1% by weight of the composition.

When the zinc X halide is formed from precursor materials, the precursor materials are preferably used in molar ratios approximately as required to produce the desired zinc X halide, although an excess of one material or another may be desirable in certain formulations, e.g., to balance pH against other formulation constituents, to provide additional antibacterial zinc, or to provide amino acid buffer. Preferably, however, the amount of halide is limited, as constraining the level of halide somewhat encourages interaction between the zinc and the amino acid. For example, in one embodiment to produce zinc lysine chloride ($ZnLysine_2Cl_2$ or $ZnLys_3Cl_2$), the molar ratios of the elements in the precursor materials would include about 1 molar equivalent $Zn^{2+}$: 3 molar equivalents Lys: 2 molar equivalents $Cl^-$.

In some embodiments, the total amount of zinc in the composition is 0.05 to 10% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, a molar ratio of zinc to amino acid is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

In certain embodiments, the composition is anhydrous. By anhydrous, there is less than 5% by weight water, optionally less than 4, less than 3, less than 2, less than 1, less than 0.5, less than 0.1 down to 0% by weight water.

In certain embodiments, the zinc X halide can have a conductivity of greater than 8000, optionally greater than 9000, greater than 10,000, or greater than 12,000 µS/cm, preferably when the pH is at least 4.

In certain embodiments, the zinc X halide is a zinc-lysine complex having the formula $[Zn(C_6H_{14}N_2O_2)_2Cl]^+Cl^-$ (sometimes referred to herein as "ZLC").

In certain embodiments, the zinc X halide has the formula $ZnX_2Hal_2$ or $ZnX_3Hal_2$, wherein Zn is a divalent zinc ion and Hal is a halide ion.

The surfactant can be any known surfactant, such as anionic surfactant, nonionic surfactant, amphoteric surfactant, zwitterionic surfactant, or cationic surfactant. The amount of surfactant can be any amount of surfactant that can be used in a cleansing composition. In certain embodiments, the amount of surfactant is 0.1 to 40% by weight of the composition. In certain embodiments, the composition contains no more than 0.1 weight % anionic surfactant.

The cleansing composition can contain any other conventional materials that are included in personal care cleansing compositions, such as liquid hand soaps, body washes, or shower gels.

EXAMPLE 1

Liquid Hand Soap with ZLC 1 g of ZLC solution (16.6% solution in deionized water, or 2.53% w/w Zn) is combined with 4 g of a commercial liquid hand soap (LHS) having a formulation as set forth in Table 1, to provide about 0.5% w/w Zn concentration in the mixture (about 3.3% ZLC complex),

TABLE 1

| Material | Weight % |
| --- | --- |
| Water and minors | Q.S. |
| Cetrimonium chloride (cetyl trimethyl ammonium chloride) | 2.4 |
| Glycerin | 2 |
| Lauramidopropyldimethylamine oxide | 1.2 |
| Cocamide MEA (cocomonoethanolamide) | 1 |
| PEG-120 methyl glucose dioleate | 0.6 |
| Myristamidopropylamine oxide | 0.4 |
| $C_{12-18}$ alkyldimethylbenzyl ammonium chloride (BKC) | 0.13 |

The LHS/ZLC solution at 0.5% zinc is clear. The LHS/ZLC solution is then diluted 2 fold, 4 fold, 8 fold, 16 fold and 32 fold, and precipitation is observed.

Optical Density (Absorbance) of LHS/ZLC is obtained and compared with original LHS via Lambda 25 UV/VIS Spectrometer (PerkinElmer) at the wavelength of 610 nm. DI water sample was used as blank; the values shown in table 1 are compared to blank. Thus, a positive number means the sample is less transparent than the blank, and negative number indicates the sample being measured appears more transparent than the blank. Both hand soap formula (original LHS and LHS/ZLC) show very similar absorbance, meaning that they have similar clarity. As the original hand soap is diluted, it becomes more transparent. When the ZLC employed hand soap formula is diluted, it initially becomes more transparent. However, as it is further diluted (16 fold and 32 fold, corresponding to about 0.03% and 0.015% zinc, or about 0.2% and 0.1% ZLC, respectively), the solution becomes cloudy, and the formation of a white precipitate is observed. The absorbance data is set forth in Table 2.

TABLE 2

| | Dilution factor | | | | | |
| --- | --- | --- | --- | --- | --- | --- |
| | 0x | 2x | 4x | 8x | 16x | 32x |
| LHS | 0.0120 | 0.0000 | −0.0120 | −0.0070 | 0.0046 | 0.0028 |
| LHS/ZLC | 0.0125 | 0.0050 | −0.0175 | −0.0186 | 0.1248 | 0.0628 |

Comparing the dilution of original liquid hand soap and the ZLC containing hand soap, the latter provides a significant signal for the phase change (from transparent to cloudy precipitation). Thus, ZLC can be incorporated into a commercial liquid hand soap and will act as a visual/sensory trigger during the washing process. In addition, the precipitate formed, ZnO, enhances the antibacterial properties of the LHS, as well as providing a skin protection benefit.

EXAMPLE 2

Liquid Hand Soap with ZLC and Anionic Surfactant 20 g of ZLC solution (2.23% w/w Zn in deionized water) is combined with 60 g of a commercial liquid hand soap (LHS) having a formulation as set forth in Table 3 to provide about 0.56% w/w Zn concentration in the mixture. The mixture is transparent.

TABLE 3

| Material | Weight % |
|---|---|
| Water and minors | Q.S. |
| C14-16 sodium alpha olefin sulfonate | 8.6 |
| Lauramide DEA | 4 |
| Sodium chloride | 1 |
| Cocamidopropyl betaine | 0.9 |
| Diethanolamine | 0.3 |
| Polyquaternium-7 | 0.04 |

The mixture was aged at 50° C. for three days and remained stable. The mixture is then diluted 2 fold, 4 fold, 8 fold, 16 fold and 32 fold, and precipitation is observed using a Turbiscan at 37° C. Turbidity is measured in one minute intervals for 45 minutes at this temperature. The results are in Table 4 below.

| t(sec) | T(t) 5 mm-45 mm (%) |
|---|---|
| 2 fold | |
| 0 | 71.63 |
| 1 | 72.05 |
| 2 | 71.02 |
| 3 | 70.1 |
| 4 | 69.27 |
| 5 | 68.49 |
| 6 | 67.67 |
| 7 | 67.05 |
| 8 | 66.34 |
| 9 | 65.56 |
| 10 | 64.84 |
| 11 | 64.23 |
| 12 | 63.66 |
| 13 | 63.06 |
| 14 | 62.46 |
| 15 | 61.92 |
| 16 | 61.43 |
| 17 | 60.95 |
| 18 | 60.54 |
| 19 | 60.09 |
| 20 | 59.67 |
| 21 | 59.28 |
| 22 | 58.92 |
| 23 | 58.56 |
| 24 | 58.25 |
| 25 | 57.9 |
| 26 | 57.59 |
| 27 | 57.27 |
| 28 | 56.98 |
| 29 | 56.68 |
| 30 | 56.4 |
| 31 | 56.13 |
| 32 | 55.86 |
| 33 | 55.59 |
| 34 | 55.34 |
| 35 | 55.08 |
| 36 | 54.86 |
| 37 | 54.64 |
| 38 | 54.42 |
| 39 | 54.2 |
| 40 | 53.99 |
| 41 | 53.82 |
| 42 | 53.6 |
| 43 | 53.4 |
| 44 | 53.21 |
| 45 | 52.99 |
| 4 fold | |
| 0 | 42.38 |
| 1 | 36.5 |
| 2 | 32.24 |
| 3 | 28.99 |
| 4 | 26.39 |
| 5 | 24.22 |
| 6 | 22.36 |
| 7 | 20.75 |
| 8 | 19.32 |
| 9 | 18.02 |
| 10 | 16.83 |
| 11 | 15.74 |
| 12 | 14.73 |
| 13 | 13.81 |
| 14 | 12.95 |
| 15 | 12.15 |
| 16 | 11.41 |
| 17 | 10.72 |
| 18 | 10.08 |
| 19 | 9.498 |
| 20 | 8.957 |
| 21 | 8.459 |
| 22 | 8.003 |
| 23 | 7.583 |
| 24 | 7.195 |
| 25 | 6.84 |
| 26 | 6.519 |
| 27 | 6.224 |
| 28 | 5.953 |
| 29 | 5.701 |
| 30 | 5.465 |
| 31 | 5.257 |
| 32 | 5.07 |
| 33 | 4.891 |
| 34 | 4.732 |
| 35 | 4.579 |
| 36 | 4.44 |
| 37 | 4.315 |
| 38 | 4.197 |
| 39 | 4.082 |
| 40 | 3.974 |
| 41 | 3.879 |
| 42 | 3.786 |
| 43 | 3.706 |
| 44 | 3.62 |
| 45 | 3.531 |
| 8 fold | |
| 0 | 61.26 |
| 1 | 57.45 |
| 2 | 54.18 |
| 3 | 51.13 |
| 4 | 48.21 |
| 5 | 45.36 |
| 6 | 42.55 |
| 7 | 39.91 |
| 8 | 37.33 |
| 9 | 34.83 |

| t(sec) | T(t) 5 mm-45 mm (%) |
|---|---|
| 10 | 32.5 |
| 11 | 30.33 |
| 12 | 28.33 |
| 13 | 26.51 |
| 14 | 24.86 |
| 15 | 23.32 |
| 16 | 21.94 |
| 17 | 20.71 |
| 18 | 19.57 |
| 19 | 18.53 |
| 20 | 17.59 |
| 21 | 16.72 |
| 22 | 15.93 |
| 23 | 15.19 |
| 24 | 14.5 |
| 25 | 13.89 |
| 26 | 13.32 |
| 27 | 12.82 |
| 28 | 12.34 |
| 29 | 11.9 |
| 30 | 11.49 |
| 31 | 11.14 |
| 32 | 10.78 |
| 33 | 10.46 |
| 34 | 10.16 |
| 35 | 9.877 |
| 36 | 9.627 |
| 37 | 9.399 |
| 38 | 9.171 |
| 39 | 8.971 |
| 40 | 8.771 |
| 41 | 8.595 |
| 42 | 8.419 |
| 43 | 8.262 |
| 44 | 8.116 |
| 45 | 7.978 |
| 16 fold | |
| 0 | 86.89 |
| 1 | 86.36 |
| 2 | 85.76 |
| 3 | 85.19 |
| 4 | 84.6 |
| 5 | 84.06 |
| 6 | 83.49 |
| 7 | 82.87 |
| 8 | 82.1 |
| 9 | 81.15 |
| 10 | 80.06 |
| 11 | 78.83 |
| 12 | 77.41 |
| 13 | 75.89 |
| 14 | 74.3 |
| 15 | 72.67 |
| 16 | 70.97 |
| 17 | 69.16 |
| 18 | 67.47 |
| 19 | 65.71 |
| 20 | 63.96 |
| 21 | 62.19 |
| 22 | 60.58 |
| 23 | 58.85 |
| 24 | 57.18 |
| 25 | 55.58 |
| 26 | 54.02 |
| 27 | 52.64 |
| 28 | 51.19 |
| 29 | 49.83 |
| 30 | 48.48 |
| 31 | 47.26 |
| 32 | 46.02 |
| 33 | 44.85 |
| 34 | 43.71 |
| 35 | 42.64 |
| 36 | 41.6 |
| 37 | 40.61 |
| 38 | 39.7 |
| 39 | 38.74 |
| 40 | 38.03 |
| 41 | 37.12 |
| 42 | 36.38 |
| 43 | 35.73 |
| 44 | 35.12 |
| 45 | 34.46 |
| 32 fold | |
| 0 | 86.84 |
| 1 | 86.59 |
| 2 | 86.32 |
| 3 | 86.1 |
| 4 | 85.88 |
| 5 | 85.7 |
| 6 | 85.52 |
| 7 | 85.33 |
| 8 | 85.18 |
| 9 | 85.03 |
| 10 | 84.9 |
| 11 | 84.78 |
| 12 | 84.66 |
| 13 | 84.55 |
| 14 | 84.45 |
| 15 | 84.36 |
| 16 | 84.29 |
| 17 | 84.22 |
| 18 | 84.16 |
| 19 | 84.09 |
| 20 | 84.04 |
| 21 | 84.01 |
| 22 | 83.99 |
| 23 | 83.96 |
| 24 | 83.93 |
| 25 | 83.91 |
| 26 | 83.89 |
| 27 | 83.89 |
| 28 | 83.86 |
| 29 | 83.83 |
| 30 | 83.83 |
| 31 | 83.81 |
| 32 | 83.8 |
| 33 | 83.79 |
| 34 | 83.77 |
| 35 | 83.76 |
| 36 | 83.75 |
| 37 | 83.74 |
| 38 | 83.74 |
| 39 | 83.73 |
| 40 | 83.72 |
| 41 | 83.71 |
| 42 | 83.71 |
| 43 | 83.7 |
| 44 | 83.69 |
| 45 | 83.68 |

ZLC can be incorporated into a commercial anionic liquid hand soap and will act as a visual/sensory trigger during the washing process.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight based on a total composition or formulation weight of 100%. The amounts given are based on the active weight of the material.

The invention claimed is:

1. A method for cleansing skin
which comprises washing skin with a liquid hand soap or body wash which provides a visual indicator of completion of the washing process and applies a zinc oxide sunscreen layer to the skin, wherein the liquid hand soap or body wash comprises a composition comprising a surfactant and a zinc X halide complex, wherein the zinc X halide complex is a zinc-lysine complex having the formula $[Zn(C_6H_{14}N_2O_2)_2Cl]^+Cl^-$, and wherein when the skin is washed with the liquid hand soap or body wash and water for a sufficient amount of time the zinc X halide complex precipitates from the liquid hand soap or body wash; and wherein the precipitate provides a visually observable zinc oxide precipitate which forms upon increase in a dilution with water; and wherein the presence of the visually observable precipitate indicates to an individual that they have washed their skin for a sufficient amount of time.

2. The method of claim 1, wherein a total amount of zinc present in the composition is 0.05 to 8% by weight.

3. The method of claim 1, wherein the zinc X halide complex is formed from a mixture of zinc oxide and lysine hydrochloride, optionally in a molar ratio of ZnO:Lysine.HCl of from 2:1 to 1:3, optionally about 1:2.

4. The method of claim 1, wherein the zinc X halide complex is made by combining zinc oxide with an amino acid hydrohalide.

5. The method of claim 1, wherein the zinc X halide complex is made by combining tetrabasic zinc chloride with an amino acid hydrohalide.

6. The method of claim 1, wherein the total amount of zinc present in the composition is 0.1 to 2% by weight of the composition.

7. The method of claim 1, wherein the surfactant comprises one or more non-ionic surfactants selected from amine oxide surfactants, alcohol amide surfactants, polyethoxylated surfactants, and combinations thereof.

8. The method of claim 1, wherein the composition is free of anionic surfactants.

9. The method of claim 1, wherein the time is 10 seconds to 60 seconds, optionally, 10 to 30 seconds, 10 to 20 seconds, or 15 to 20 seconds.

10. The method of claim 1, wherein the precipitate is a zinc salt and the zinc salt adheres to the skin and protects the skin from sun damage prior to exposure to the sun.

11. The method according to claim 1, wherein the composition is anhydrous.

* * * * *